United States Patent [19]

Huisman

[11] Patent Number: 5,212,154
[45] Date of Patent: May 18, 1993

[54] PREPARATION FOR TREATING COMPLICATIONS IN DIABETES

[75] Inventor: Robby Huisman, Grave, Netherlands

[73] Assignee: Akzo N.V., Velperweg, Netherlands

[21] Appl. No.: 887,577

[22] Filed: May 19, 1992

Related U.S. Application Data

[63] Continuation of Ser. No. 225,452, Jul. 28, 1988, abandoned.

[30] Foreign Application Priority Data

Aug. 14, 1987 [NL] Netherlands .......................... 8701912

[51] Int. Cl.$^5$ ...................... A61K 37/26; A61K 37/02
[52] U.S. Cl. .......................................... 514/4; 514/17; 514/866; 514/951; 514/953; 514/964; 514/3; 514/12; 530/329; 530/303; 424/422; 424/423; 424/485; 424/486; 930/10; 930/20; 930/21
[58] Field of Search .................. 514/3, 4, 12, 17, 866, 514/951, 953, 964; 530/329, 303, 304; 424/422, 423, 485, 486

[56] References Cited

U.S. PATENT DOCUMENTS

| | | |
|---|---|---|
| 3,773,919 | 11/1973 | Boswell ............................... 424/422 |
| 4,110,322 | 8/1978 | Greven ................................ 530/327 |
| 4,675,189 | 6/1987 | Kent ..................................... 930/21 |

FOREIGN PATENT DOCUMENTS

| | | |
|---|---|---|
| 0052510 | 5/1982 | European Pat. Off. . |
| 0058481 | 8/1982 | European Pat. Off. . |
| 0303308 | 2/1989 | European Pat. Off. . |
| 2104382A | 3/1983 | United Kingdom . |

OTHER PUBLICATIONS

Conn's "Current Therapy" Edited by H. F. Conn., M.D., 1966, W. B. Saunders Co., Philadelphia, p. 610.
Halonen, Eur. J. Appl. Physiol., 54, 647-655 (1986).
Elderson et al. J. of The Neurological Sciences, 93, 167-174 (1989).
Roelofs et al. Neurology, 34, 934-938 (1984).
Conn's "Current Therapy" Edited by Robert E. Rankel, M.D., 1989, W. B. Saunders Co. pp. 489-490.

Primary Examiner—F. T. Moezie
Attorney, Agent, or Firm—William M. Blackstone

[57] ABSTRACT

Preparation for preventing or combating complications in diabetes, characterized in that it comprises:
(a) insulin or a salt or complex thereof, and
(b) a peptide of the general formula I:

H-L-Met(X)-L-Glu-L-His-L-Phe-D-Lys-L-Phe-Y or a salt or a N-acyl derivative thereof, wherein
Met(X) represents the amino acid radical Met, Met(O) or Met(O$_2$),
Y represents the group Gly-Z or Z, and
Z represents the hydroxyl group, an esterified hydroxyl group or a substituted or unsubstituted amino group.

7 Claims, No Drawings

PREPARATION FOR TREATING COMPLICATIONS IN DIABETES

This is a continuation application of U.S. Ser. No. 07/225,452, filed Jul. 28, 1988 now abandoned.

The present invention relates to a pharmaceutical preparation for combating or preventing complications in diabetes mellitus.

Diabetes mellitus is primarily characterized by a reduction or cessation of the ability to oxidize carbohydrates, resulting in partial or complete disturbance of the normal insulin mechanism.

In diabetes mellitus patients there furthermore regularly arise, especially after a longer period, complications which can be of a sensory, autonomous or, to a lesser extent, motor type. These complications, in general also called diabetic neuropathies, relate to a very heterogeneous and frequently also mutually overlapping group of neurological syndromes, and as a rule arise not withstanding the fact that the blood sugar level is kept within reasonable limits by treatment with insulin. In a number of cases the abovementioned complications have proved irreversible, so that the patient naturally benefits if the complications in question do not arise at all.

Sensory complications often manifest themselves in the form of pain, autonomous complications in the form of, inter alia, organic impotence and orthostatic hypotension, and motor complications in the form of muscular weakness.

Some of these complications can be eliminated with greater of lesser success by a highly balanced and excellently controlled administration of insulin. However, such treatment is in many cases not possible and is anyhow highly patient-unfriendly.

According to some experts, a possible cause of these neurological complications in diabetes mellitus is thought to be the formation of sorbitol, resulting from glucose with the aid of the enzyme aldose reductase. Hence, the administration of aldose reductase inhibitors is proposed as a possible method of treatment for combating these diabetes mellitus complications The present invention provides a pharmaceutical preparation for combating or preventing complications in patients with diabetes, which keeps the blood sugar level within reasonable limits and at the same time combats or prevents the neurological complications.

The preparation according to the invention comprises:
(a) insulin or a salt or complex thereof, and
(b) a peptide of the general formula I:

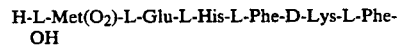

or a salt or a N-acyl derivative thereof, wherein

Met(X) represents the amino acid radical Met, Met(O) or Met(O$_2$),

Y represents the group Gly-Z or Z, and

Z represents the hydroxyl group, an esterified hydroxyl group or a substituted or unsubstituted amino group.

As the insulin, it is in principle possible to use any insulin, crystalline or amorphous, insulin of animal origin or produced with the aid or recombinant DNA techniques or by synthetic or semisynthetic methods of preparation.

Depending on the requirements of the individual patient it is, moreover, possible to choose a quick-acting insulin form or slower-acting insulin forms, with the latter in general consisting to a greater or lesser degree of insulin-zinc complexes or protamineinsulin complexes.

Peptides of the general formula I are known peptides. Concerning the preparation of such peptides reference is made, for brevity, to U.S. Pat. No. 3,842,064 and European Patent Application 179,332. These peptides are in particular known for their psychopharmacological action.

Peptides according to formula I which are preferably used within the scope of the present invention, are those wherein Met(X) represents the amino acid Met(O$_2$), (methioninesulphone) and Y represents a hydroxyl group, a hydroxyl group which is esterified with an aliphatic alcohol having 1 to 18 carbon atoms (and preferably a lower aliphatic alcohol having 1 to 6 carbon atoms) or a substituted amino group of the type —NH—ALK—NH$_2$, wherein ALK represents an alkylene group with 2 to 10 carbon atoms, preferably 4 to 10 and more especially 7 or 8 carbon atoms.

A peptide having the formula II:

(II)

or a salt thereof is more especially preferred within the scope of the present invention.

By N-acyl derivatives of the peptides of formula I refers to peptides I which are acylated at the N-terminal side with a lower (1–8 C) aliphatic monocarboxylic acid or dicarboxylic acid, such as acetic acid, propionic acid, butyric acid, malonic acid, succinic acid or glutaric acid.

The pharmaceutical preparation according to the invention is preferably administered subcutaneously or intranasally.

For subcutaneous administration in the form of an intramuscular or intravenous injection preparation, the two peptides concerned, namely insulin and the peptide according to formula I, are dissolved, suspended or emulsified in a liquid suitable for injection. A solution of the two peptides in water is, however, preferred in this context.

For subcutaneous administration in the form of an infusion, the peptides are dissolved, at a concentration suitable for infusion, in a pharmaceutically acceptable solvent, preferably water. Such a solution of the peptides in question can be administered in so-called osmotic insulin pumps or insulin pumps working by different mechanisms.

An outstandingly suitable subcutaneous administration form is furthermore a so-called implant, a subcutaneous depot from which an effective quantity of the two peptides is released in a controlled manner and over a lengthy period. By implant there is here understood a subcutaneous administration form, wherein the peptides in question are dispersed in a suitable polymer or are encapsulated by such a polymer, and wherein the peptides are present in a quantity which is greater than is necessary for a normal injection dosage.

Very suitable implants which can function as subcutaneous depots are the so-called microcapsules, microspheres or microgranules, which can conveniently be injected subcutaneously with the aid of a liquid. Larger shapes such as granules or "rods" can also be used. The larger dimensions and thus more troublesome introduction procedure of the latter depot forms are often more than compensated for by the convenient removablilty of this type of implant.

Suitable polymers which can be used for these implants are, inter alia, polysiloxanes, polyalkylenes such as polyethylene and polypropylene and above all the so-called biological degradable polymers among which the polylactides (including copolymers thereof) occupy a leading place. Methods for producing such implants are extensively described in the literature; for brevity, reference is made in this context to the content of, for example, U.S. Pat. No. 3,773,919 published European Patent Applications 52,510 and 58,481.

In this specification, the term "polylactide" is used in a generic sense to include polymers of lactic acid alone, copolymers of lactic acid and glycolic acid, mixtures of such polymers, mixtures of such copolymers, and mixtures of such polymers and copolymers, the lactic acid being either in racemic or in optically active form (EP 58,482 A1, page 2, lines 21-27).

Thus, according to the present invention, there is provided a pharmaceutical composition comprising a polylactide, as hereinbefore defined, and an acid-stable polypeptide, which, when placed in an aqueous physiological-type environment, releases polypeptide into said aqueous physiological-type environment in a continuous manner, as hereinbefore defined until essentially all of the polypeptide has been released (EP 58,481 A1, page 4, lines 18-25).

Suitable solid compositions for sub-dermal injection or implantation are, for example, rods, spheres, films or pellets, and cylindrical rods which can be injected through a hypodermic needle or trochar are preferred (EP 58,481 A1, page 18, lines 24-28).

Also as indicated above, the composition of the invention may also be formulated as a suspension for injection. Such suspensions may be manufactured by general techniques well known in the pharmaceutical art, for example by milling the polylactide/polypeptide mixture in an ultracentrifuge mill fitted with a suitable mesh screen, for example a 120 mesh, and suspending the milled, screened particles in a solvent for injection, for example propylene glycol, water optionally with a conventional viscosity increasing or suspending agent, oils or other known, suitable liquid vehicles for injection (EP 58,481 A1, page 20, lines 2-13).

Thus, according to a further feature of the invention there is provided a suspension formulation comprising from 1 to 50% by weight of a solid formulation, which itself comprises from 0.1 to 50% by weight of an acid-stable polypeptide as herein defined and from 50 to 99.9% by weight of a polylactide wherein the ratio of glycolide to lactide units is 0 to 3 and which is either soluble in benzene and has an inherent viscosity (1 g./100 ml. solution in benzene) of less than 0.5 or is insoluble in benzene and has an inherent viscosity (1 g./100 ml. solution in chloroform or dioxan) of less than 4, which solid formulation has been reduced to fine particle size, together with from 50 to 99% by weight of a liquid carrier suitable for injection into mammals.

It is to be noted that, because of the reduced particle size of the polypeptide/polylactide in a suspension for injection, certain solid formulations, which are not suitable for implantation, are rendered useful when reduced to fine particle size and formulated as a suspension for injection (EP 58,481 A1, page 21, line 20 to page 22, line 6).

From the foregoing, it is clear that it is desirable to manufacture polylactides of a range of $M_w$, particularly of low to medium $M_w$ in the range up to 60,000, and of high polydispersity $M_w/M_n$, these being particularly valuable in the compositions of this invention (EP 58,481 A1, page 22, lines 14-16).

We have realised that, because of the different reactivities under polymerisation conditions of the cyclic dimers of lactic acid and glycolic acid, copolymers of high heterogeneity in respect of polymer species may be obtained by ring opening polymerisation of a mixture of the two cyclic dimers in the presence of chain-stopping agents, to give polylactides having an inherent viscosity of less than 0.5. The cyclic dimer of glycolic acid is the more reactive under polymerisation conditions, and thus the first copolymer molecules formed in the polymerisation are glycolic acid-rich. Consequentially, the later copolymer molecules formed are necessarily lactic acid-rich, thus producing a copolymer of lactic acid and glycolic acid of the desired high heterogeneity.

In addition, we control the polymerisation to produce copolymers in the desired low $M_w$ range by carrying out the ring opening copolymerisation of the mixed cyclic dimers in the presence of water, of lactic acid containing water, or of some other known chain growth regulator, in accordance with the general knowledge in the polymer art.

Suitable polymerisation catalysts are zinc oxide, zinc carbonate, basic zinc carbonate, diethylzinc, organotin compounds, for example stannous octanoate, tributylaluminum, titanium, magnesium or barium compounds, or litharge, and of these stannous octanoate is preferred.

The copolymerisation of the mixed cyclic dimers is otherwise carried out in conventional manner, known in the polymer art, as regards time and temperature.

Low molecular wight polylactides may also be obtained by copolymerisation of the hydroxy-acids themselves rather than the cyclic dimers (EP 58,481 A1, page 22, line 26 through page 23, line 29).

The lactic acid content of the copolymer is preferably in the racemic (D,L) form, or in the optically active L form (EP 58,481 A1, page 25, lines 25-27).

The compositions of this invention are hormonally active microcapsule formulations comprising at least one hormonally active polypeptide and optionally a polymer hydrolysis modifying agent intimately mixed with or coated by a biocompatable, biodegradable polymer which, when administered to a mammal, will release a daily amount of polypeptide effective for maintaining an hormonally related condition over a predetermined period of time (EP 52,510 A2, page 2, line 16-25).

One or more polymer hydrolysis modifying agents may optionally be present in these compositions. These agents, when present, may decrease or increase the rate of polymer hydrolysis. They are low molecular weight non-toxic organic acids, neutral or basic salts (EP 52,510 A2, page 2, lines 31-35).

Optionally, certain chemicals which affect the rate of polymer hydrolysis may be dissolved in the aqueous solution containing the polypeptide before it is encapsulated by the polymer excipient. These chemicals are called polymer hydrolysis modifying agents. When present, these compounds may increase or decrease the rate at which the drug is released from the microcapsules. This affect is independent of a particular polymer composition or size.

Four types of chemicals may be used to realize this effect, for example, organic acids, acidic neutral or basic salts. Low molecular weight mono and dicarboxylic acids such as acetic acid, tartaric acid, citric acid, gluconic acid, oxalic acid, ascorbic acid, succinic acid, their salts, and the like may be used. Basic salts may be, for example, ammonium sulfate, ammonium chloride, ammonium nitrate, sodium bisulphate and the like. Neutral salts effective herein include metal halides such as, for example, sodium chloride, potassium chloride, sodium bromide, potassium bromide, calcium chloride, sodium bromide, potassium bromide, calcium chloride, magnesium chloride and the like. Basic salts include such salts as sodium carbonate, potassium carbonate, trisodium phosphate, tripotassium phosphate and the like. Of these compounds it is most preferred to use either citric acid, sodium chloride or sodium carbonate. Combinations of these compounds will achieve the desired affect but the compositions described herein contain only one of these agents in a particular composition.

When present the hydrolysis modifying agent will be added in an amount between 0.1 and 20% by weight of the polymer but preferably it will be present in the amount of 5 to 10%.

The number and type of encapsulating excipients which may be effectively used to practice this invention is limited only by the requirements that the material be biocompatable and biodegradable. That is, the polymer must be non-toxic to the host and must be of such composition that it is degradable by the body into metabolic products that have no deleterious or untoward effects on the body. These polymers must also be capable of forming microcapsules containing water-soluble drugs (EP 52,510 A2, page 10, line 6 through page 11, line 11).

The encapsulating material is a synthetic polymer comprising certain poly($\alpha$-hydroxycarboxylic acids), poly(lactones), poly(acetals), poly(orthoesters) or poly(orthocarbonates).

The process for preparing these compositions is also disclosed, which process involves phase-separation techniques whereby the encapsulating polymer is precipitated onto water droplets containing the peptide and hydrolysis modifying agent, dispersed as in water-in-oil emulsion, by the addition of a coacervation agent which is a non-solvent for the encapsulating polymer. The capsules are then hardened, washed and dried (EP 52,510 A2, page 3, line 1–14).

A number of polymers have been developed which meet these criteria. Various combinations of alpha hydroxy-carboxylic acids and certain lactones can be condensed to form such polymers, particularly lactic acid and glycolic acid or combinations thereof. See, for example U.S. Pat. No. 3,773,919. Similar biocompatable polymers based on glycolic acid and glycerol and the like also are known. See U.S. Pat. Nos. 3,991,776; 4,076,779 and 4,118,470 for examples of such compositions. Several new biocompatable, biodegradable polymers derived from polyorthoesters and polyorthocarbonates also may be effectively used as encapsulating excipients in the practice of this invention. These latter polymers are described in U.S. Pat. Nos. 4,093,709 and 4,138,344. there are also known polyacetals and polyorthoesters useful for this purpose as described in Polymer Letters 18, 293 (1980). this list is not intended to be exhaustive of the polymers which are compatable with the scope and intention of this invention but merely sets out examples to illustrate the type of polymer excipients which may be used.

One preferred group of polymer excipients are the orthoester and orthocarbonate polymers having a repeating mer comprising a hydrocarbon radical and a symmetrical dioxycarbon of the general formula:

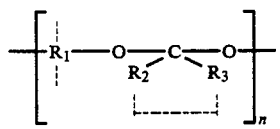

wherein $R_1$ is a multivalent hydrocarbon radical, $R_2$ and $R_3$ are hydrocarbon radicals with at least one of $R_2$ or $R_3$ bonded to the dioxycarbon through the oxygen linkage, and which polymers are synthesized by reacting a polyol with an orthoester or orthocarbonate. A full and complete description of the exact compositions, preparation, and properties of these polymers can be found in U.S. Pat. Nos. 4,093,709 and 4,138,344, which are incorporated by reference as if fully set out herein.

Also preferred are those polymers based on the condensation of divinyl ethers and polyols. These compounds are prepared by reacting polyol with a diketene acetal to form the polyacetal. A more detailed description and discussion of these polymers can be found in the journal Polymer Letters, J. Heller, et al, 18, 293 (1980), which is incorporated herein by reference. Of similar interest are those polyorthoesters prepared by a modification of the synthesis used to prepare the above polyacetals. These polymers are comprised of diketene acetaldiol condensates. For example, the diketene acetal, 3,9-bis-(methylene)-2,4,-8,10-tetr-aoxaspiro[5,5]undecane can be condensed with 1,6-hexanediol to give a polyorthoester polymer which has degradation properties in vivo which make its use in the compositions of this invention desirable. Further preparation techniques and polymer characteristics for these compounds can be found in U.S. Pat. Nos. 4,093,709; 4,131,648; 4,138,344; and 4,180,646 all of which are incorporated herein by reference (EP 52,510 A2, page 11, line 12 through page 13, line 2).

The compositions of this invention will contain the hormonally active polypeptides in varying amounts depending upon the effect desired (EP 52,510 A2, page 9, lines 14–17).

The compositions of this invention are formulated to contain the polypeptide in an amount which may vary between 0.01 and 40.0 weight % of the polymer used for encapsulation. Preferably the peptide will be present in the amount between 0.1 to 10.0 weight %.

The amount of drug placed in a particular formulation depends not only on the desired daily dose but also on the number of days that dose level is to be maintained. While this amount can be calculated empirically the actual dose delivered is a function of the degradation characteristics of the encapsulating polymer. Therefore, the % weight of drug stated represent amounts which, when taken in conjunction with a particular polymer provide the desired release profile (EP 52,510 A2, page 9, line 27 through page 10, line 5).

It is furthermore obvious that a subcutaneous implant according to the present invention is not only relevant to a polymer wherein both peptides (insulin and the peptide according to formula I) are contained, but also—and even preferably—is relevant to a mixture of two types of microcapsules or other forms, wherein exclusively insulin is contained in one type and exclusively the peptide according to formula I is contained in the other type.

For intranasal administration, the two peptides in question are introduced into a medium suitable for intranasal administration and are administered by means of a propellant gas or spray mechanism.

The dosages of the two peptides in the preparation according to the invention depend greatly on the individual requirement of the diabetic patient.

In general, however, the subcutaneous injection preparation according to the invention contains between 10 and 100 international units of insulin per ml and preferably 20, 30 or 40 international units per ml.

The amount of the peptide according to the general formula I depends on the duration of action of the chosen insulin, but this peptide is preferably present in this preparation in a quantity of $10^{-4}$ to $2 \times 10^{-2}$ mmol per ml and more especially between $0.4 \times 10^{-3}$ and $7.5 \times 10^{-3}$ mmol per ml.

An outstandingly suitable injection preparation according to the invention contains between 20 and 45 international units of insulin per milliliter and between 0.35 and 6.5 mg of the peptide according to formula II (molecular weight 870) per milliliter.

Whenever the molecular weight of the peptide to be administered, of the formula I, is higher or lower than that of the abovementioned peptide of formula II, the stated preferred dosage must then be adopted correspondingly.

The amount of the injection preparation according to the invention to be administered daily depends largely on the individual condition of the patient, but will in general vary between 0.5 ml and 2 to 3 ml per day.

It is obvious that for infusion liquids and especially for implants different quantities of peptide have to be used. These quantities are, however, generally so chosen that the dosage of the two peptides in question which is to be administered daily broadly corresponds to the daily dosage described above (of the peptides in question) when administered in the form of one or more injections.

In addition to the abovementioned peptides, the preparation according to the invention can also contain other substances, with particular consideration given to:

antimicrobial substances, such as methyl parahydroxybenzoate, substances for rendering the preparation according to the invention isotonic, and substances which can adjust the pH of an aqueous solution of the preparation according to the invention.

Furthermore the pH, is preferably adjusted to a pH of between 7 and 7.8; a slightly acidic pH can, however, also readily be used.

The preparation according to the invention is further illustrated by reference to the following example.

A solution containing the following per milliliter is prepared:

| | |
|---|---|
| The peptide of formula II | 3.0 mg |
| Insulin | 40 IU |
| Methyl parahydroxybenzoate | 1 mg |
| Sodium acetate trihydrate | 1.36 mg |
| Sodium chloride | 7 mg |
| Hydrochloric acid and sodium hydroxide to give pH | 7.35 |
| Water for injection to give | 1 ml |

I claim:

1. A preparation for treating sensory diabetic neuropathies, comprising (a) from about 10 to about 100 international units of insulin per milliliter of preparation and (b) from about 0.35 to about 6.5 milligrams of a peptide of the formula:

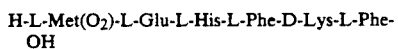

or a salt thereof per milliliter of preparation.

2. Preparation according to claim 1, comprising per ml, 40 international units of insulin and 0.35–6.5 mg of the peptide.

3. A subcutaneous implant comprising a preparation for treating sensory diabetic neuropathies according to claim 1, wherein said subcutaneous implant release in a 24-hour period in an aqueous physiological environment: (a) from about 10 to about 100 international units of insulin and (b) from about 0.35 to abut 6.5 milligrams of a peptide of the formula:

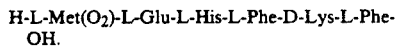

4. The implant of claim 3, comprising microcapsules, microspheres, or microgranules.

5. The implant of claim 4, comprising a mixture of microcapsules containing insulin and microcapsules containing the peptide.

6. A method of treating sensory complications in diabetes comprising administering to a diabetic patient in need of said treatment from about 0.35 to about 6.5 milligrams of the peptide of the formula:

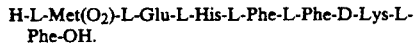

7. The method according to claim 6, wherein said peptide is co-administered with insulin.

* * * * *